(12) United States Patent
Mishra

(10) Patent No.: US 7,678,780 B2
(45) Date of Patent: Mar. 16, 2010

(54) METHOD OF TREATING CANCER USING PLATELET RELEASATE

(75) Inventor: Allan Mishra, 340 August Cir., Menlo Park, CA (US) 94025

(73) Assignee: Allan Mishra, Menlo Park, CA (US)

( * ) Notice: Subject to any disclaimer, the term of this patent is extended or adjusted under 35 U.S.C. 154(b) by 386 days.

(21) Appl. No.: 10/581,577

(22) PCT Filed: Dec. 23, 2004

(86) PCT No.: PCT/US2004/043088

§ 371 (c)(1),
(2), (4) Date: Jun. 2, 2006

(87) PCT Pub. No.: WO2005/065242

PCT Pub. Date: Jul. 21, 2005

(65) Prior Publication Data

US 2007/0184029 A1  Aug. 9, 2007

Related U.S. Application Data

(60) Provisional application No. 60/533,415, filed on Dec. 29, 2003, provisional application No. 60/533,367, filed on Dec. 29, 2003.

(51) Int. Cl.
*A01N 57/36* (2006.01)
*A01N 43/04* (2006.01)
*C12P 33/16* (2006.01)
*A35K 33/14* (2006.01)

(52) U.S. Cl. .......................... 514/120; 514/44; 435/55; 424/532

(58) Field of Classification Search ........................ None
See application file for complete search history.

(56) References Cited

U.S. PATENT DOCUMENTS

| | | | |
|---|---|---|---|
| 4,663,289 A | 5/1987 | Veech | |
| 4,931,395 A | 6/1990 | Griffin | |
| 5,079,236 A | 1/1992 | Drizen et al. | |
| 5,124,316 A | 6/1992 | Antoniades et al. | |
| 5,147,776 A | 9/1992 | Koerner, Jr. | |
| 5,165,938 A | 11/1992 | Knighton | |
| 5,178,883 A | 1/1993 | Knighton | |
| 5,385,937 A | 1/1995 | Stamler et al. | |
| 5,403,272 A | 4/1995 | Deniega et al. | |
| 5,449,688 A | 9/1995 | Wahl et al. | |
| 5,474,891 A | 12/1995 | Murphy | |
| 5,494,590 A | 2/1996 | Smith et al. | |
| 5,510,102 A | 4/1996 | Cochrum | |
| 5,578,565 A | 11/1996 | Chao et al. | |
| 5,585,007 A | 12/1996 | Antavich et al. | |
| 5,599,558 A * | 2/1997 | Gordinier et al. ........... 424/532 |
| 5,614,204 A | 3/1997 | Cochrum | |
| 5,643,786 A | 7/1997 | Cohen et al. | |
| 5,788,662 A | 8/1998 | Antanavich et al. | |
| 5,834,418 A | 11/1998 | Brazeau et al. | |
| 5,905,142 A | 5/1999 | Murray | |
| 5,935,850 A | 8/1999 | Clark et al. | |
| 6,098,631 A | 8/2000 | Holoshitz et al. | |
| 6,183,442 B1 | 2/2001 | Athanasiou et al. | |
| 6,214,338 B1 | 4/2001 | Antanavich et al. | |
| 6,242,594 B1 | 6/2001 | Kelly | |
| 6,280,473 B1 | 8/2001 | Lemperle et al. | |
| 6,315,992 B1 | 11/2001 | Noh et al. | |
| 6,322,785 B1 | 11/2001 | Landesberg et al. | |
| 6,432,119 B1 | 8/2002 | Saadat | |
| 6,454,804 B1 | 9/2002 | Ferree | |
| 6,712,851 B1 | 3/2004 | Lemperle et al. | |
| 6,811,777 B2 | 11/2004 | Mishra | |
| 6,905,612 B2 | 6/2005 | Dorian et al. | |
| 2001/0031978 A1 | 10/2001 | Kipke et al. | |
| 2002/0006437 A1 | 1/2002 | Grooms et al. | |
| 2002/0032155 A1 | 3/2002 | Ferree | |
| 2002/0058030 A1 | 5/2002 | Monroy et al. | |
| 2002/0082220 A1 | 6/2002 | Hoemann et al. | |
| 2003/0116512 A1 | 6/2003 | Delbert Antwiller et al. | |
| 2003/0152639 A1 | 8/2003 | Britton et al. | |
| 2003/0185812 A1 | 10/2003 | Ferree | |
| 2003/0192554 A1 | 10/2003 | Ferree | |
| 2003/0205538 A1 | 11/2003 | Dorian et al. | |

(Continued)

FOREIGN PATENT DOCUMENTS

EP   0 142 339   5/1985

(Continued)

OTHER PUBLICATIONS

Ozek et al. (Journal of Burn Care and Rehabilitation, pp. 65-69, Jan./Feb. 2001).*

(Continued)

*Primary Examiner*—Robert B. Mondesi
*Assistant Examiner*—Khatol Shahnan-Shah
(74) *Attorney, Agent, or Firm*—Knobbe, Martens, Olson & Bear, LLP

(57) ABSTRACT

Platelets are concentrated from the blood of a patient. The platelets are treated by a method such as ultrasound or agitation to obtain platelet releasate. This releasate as a whole or a component thereof is formulated into an injectable formulation which is administered to the same patient the platelets were extracted from in order to treat the patient's cancer.

7 Claims, 2 Drawing Sheets

U.S. PATENT DOCUMENTS

| | | | |
|---|---|---|---|
| 2003/0236573 A1* | 12/2003 | Evans et al. ............... | 623/23.58 |
| 2004/0126885 A1 | 7/2004 | Cines et al. | |
| 2004/0182795 A1 | 9/2004 | Dorian et al. | |
| 2004/0220101 A1 | 11/2004 | Ferree | |
| 2004/0220102 A1 | 11/2004 | Ferree | |
| 2004/0244806 A1 | 12/2004 | Ferree | |
| 2005/0043738 A1 | 2/2005 | Ryan | |
| 2005/0064042 A1 | 3/2005 | Vunjak-Novakovic et al. | |
| 2005/0186193 A1 | 8/2005 | Mishra | |
| 2006/0029578 A1 | 2/2006 | Hoemann et al. | |
| 2006/0041243 A1 | 2/2006 | Nayak et al. | |
| 2006/0127382 A1 | 6/2006 | Mishra | |
| 2006/0235306 A1 | 10/2006 | Cotter et al. | |
| 2006/0263407 A1 | 11/2006 | Mishra | |
| 2007/0014784 A1 | 1/2007 | Nayak et al. | |
| 2007/0037737 A1 | 2/2007 | Hoemann et al. | |
| 2007/0042016 A1 | 2/2007 | Nayak et al. | |
| 2007/0110737 A1 | 5/2007 | Mishra | |
| 2007/0122906 A1 | 5/2007 | Mishra | |

FOREIGN PATENT DOCUMENTS

| | | |
|---|---|---|
| EP | 0 417 818 | 3/1991 |
| WO | WO 00/01427 | 1/2000 |
| WO | WO 03/015800 | 2/2003 |
| WO | WO 2004/022078 | 3/2004 |
| WO | WO 2005/065242 | 7/2005 |

OTHER PUBLICATIONS

Snyder, et al. "Calcium-Dependent Proteolysis of Actin During Storage of Platelet Concentrates," *Blood*, vol. 73, No. 5, pp. 1380-1385, 1989.

Tang, et al., "The Effects of pCO2 and pH on Platelet Shape Change and Aggregation for Human and Rabbit Platelet-Rich Plasma," *Thrombosis Research*, vol. 10, No. 1, pp. 135-145, 1977.

Feuerstein, et al. "Congestive Heart Failure and Genomic Medicine: A Look into the $21^{st}$ Century," *Cardiovascular Drugs and Therapy*, vol. 11, No. 6, 713-717, 1997.

Knebel, et al. "Heart Failure: State of the Art Treatment and Options," *Clinical Nephrology*, vol. 60, Suppl. 1, pp. S59-S66, 2003.

McCarthy, "New Surgical Options for the Failing Heart," *Journal of Heart Valve Disease*, vol. 8, No. 5, pp. 472-475, 1999.

Shim, et al. "Stem Cell Cardiomyoplasty: State of the Art," *Annals of the Academy of Medicine*, Singapore, vol. 33, No. 4, pp. 451-460, 2004.

Coller, et al. "The pH Dependence of Quantitative Ristocetin-Induced Platelet Aggregation: Theoretical and Practical Implications—A New Device for Maintenance of Platelet-Rich Plasma pH," *Blood*, vol. 47, No. 5, pp. 841-854, May 1976.

Gruber, et al. "Platelets Stimulate Proliferation of Bone Cells: Involvement of Platelet-Derived Growth Factor, Microparticles and Membranes," *Clin. Oral Impl. Res.*, vol. 13, pp. 529-535, 2002.

Marx, et al. "Platelet-Rich Plasma, Growth Factor Enhancement for Bone Grafts," *Oral Surgery Oral Medicine Oral Pathology*, vol. 85, No. 6, pp. 638-646, Jun. 1998.

Cohen, et al. "Wound Care and Wound Healing," in *Principles of Surgery*, Chapter 8 (Seymore, et al. eds.) pp. 263-295, New York, 1999.

Barrett, et al. "Growth Factors for Chronic Plantar Fasciitis?" *Podiatry Today*, pp. 37-42, Nov. 2004.

Edwards, et al. "Autologous Blood Injections for Refractory Lateral Epicondylitis," *The Journal of Hand Surgery*, pp. 272-278, vol. 28A, No. 2, Marc, 2003.

Eppley, et al. "Platelet Quantification and Growth Factor Analysis from Platelet-Rich Plasma: Implications for Wound Healing," *Plastic and Reconstructive Surgery*, pp. 1502-1508, vol. 114, No. 6, Nov. 2004.

Kahn, et al. "Overuse Tendinosis, Not Tendinitis, Part 1: A New Paradigm for a Difficult Clinical Problem," *The Physician and Sportsmedicine*, vol. 28, No. 5, 8 pages, May 2000.

Cook, et al. "Overuse Tendinosis, Not Tendinitis, Part 2: Applying the New Approach to Patellar Tendinopathy," *The Physician and Sportsmedicine*, vol. 28, No. 6, 12 pages, Jun. 2000.

Khan, et al. "Histopathology of Common Tendinopathies: Update and Implications for Clinical Management," *Clinical Sports Medicine*, vol. 27, No. 6, 1999.

Price, et al. "Local Injection Treatment of Tennis Elbow—Hydrocortisone, Triamcinolone and Lignocaine Compared," *British Journal of Rheumatology*, vol. 30, pp. 39-44, 1991.

Taylor, et al. "The Response of Rabbit Patellar Tendons After Autologous Blood Injection," *Medicine & Science in Sports & Exercise*, vol. 34, No. 1, pp. 70-73, 2001.

Floryan, et al. "Home Study Program: Intraoperative Use of Autologous Platelet-Rich and Platelet-Poor Plasma for Orthopedic Surgery Patients," *Aorn Journal*, vol. 80, No. 4, pp. 667-678, Oct. 2004.

Balk, et al. "Outcome of Surgery for Lateral Epicondylitis (Tennis Elbow): Effect of Worker's Compensation," *The American Journal of Orthopedics*, pp. 122-126, Mar. 2005.

Harvest Technologies GmbH Brochure for SmartPReP 2, 2002.

Website download from Medtronic, "Magellan" System Features and Benefits, 3 pages, 2004.

Cell Factor Technologies, Inc., Brochure for GPS II Platelet Concentrate System, 10 pages, 2004.

Cell Factor Technologies, Inc., Brochure for Boost Demineralizedbonematrix, 6 pages, 2004.

DePuy AcroMed, Inc. Brochure for Symphony Platelet Concentrate System, 10 pages, 2001.

Cotter, et al. "A Novel Method for Isolation of Neutrophils from Murine Blood Using Negative Immunomagnetic Separation," *The American Journal of Pathology*, vol. 159, pp. 473-481, 2001.

Yang, et al. "Dielectric Properties of Human Leukocyte Subpopulations Determined by Electrorotation as a Cell Separation Criterion," *Biophysical Journal*, vol. 76, pp. 3307-3314, Jun. 1999.

Martinez-Gonzalez, et al. "Do Ambulatory-Use Platelet-Rich Plasma (PRP) Concentrates Present Risks," *Medicina Oral*, vol. 7, pp. 375-390, 2002.

International Search Report dated May 9, 2006.

* cited by examiner

Human Fibroblast Proliferation

METHOD OF TREATING CANCER USING PLATELET RELEASATE

CROSS-REFERENCE TO RELATED APPLICATIONS

This application is the U.S. National Phase under 35 U.S.C. §371 of International Application PCT/US04/043088, filed Dec. 23, 2004, which claims priority to U.S. Provisional Application No. 60/533,415, filed Dec. 29, 2003 and U.S. Provisional Application No. 60/533,367, filed Dec. 29, 2003.

FIELD OF THE INVENTION

This invention relates generally to the field of medicine and more particularly to formulations and methods of treating cancer.

BACKGROUND OF THE INVENTION

Formulations and methods of the invention can be applied to the treatment of a variety of different diseases and abnormalities. Although the present invention is not limited to such, it can be used in the treatment of cancer, wound healing, and a variety of chronic inflammatory diseases. In general, each is presently treated directly by physical means such as surgical removal of cancerous tissue, suturing of wounds and surgical removal of inflamed joints. Further, each can be treated by chemical means. Chemotherapy is applied to cancers, growth hormones are applied to wound healing and anti-inflammatory drugs are applied to treating chronic inflammatory conditions. These, and related treatments are directed, in general, to treating the cancerous, injured, or inflamed tissue using active compounds not native to the patient's body. The present invention can be used along with all or any of these treatments. However, in order to provide an understanding on how the present invention departs from conventional treatment modalities a brief and general description of current treatment technologies in these areas is provided.

Cancer Treatments

The term "cancer" encompasses a spectrum of diseases that vary in treatment, prognosis, and curability. The approach to diagnosis and treatment depends on the site of tumor origin, the extent of spread, sites of involvement, the physiologic state of the patient, and prognosis. Once diagnosed, the tumor is usually "staged," a process which involves using the techniques of surgery, physical examination, histopathology, imaging, and laboratory evaluation to define the extent of disease and to divide the cancer patient population into groups in order of decreasing probability of cure. Such systems are used both to plan treatment and determine the prognoses for the patient (Stockdale, F., 1996, "Principles of Cancer Patient Management," In: Scientific American Medicine, vol. 3, Dale, D. C., and Federman, D. D. (eds.), Scientific American Press, New York).

The type or stage of the cancer can determine which of the three general types of treatment will be used: surgery, radiation therapy, and chemotherapy. An aggressive, combined modality treatment plan can also be chosen. To this end, surgery can be used to remove the primary tumor, and the remaining cells are treated with radiation therapy or chemotherapy (Rosenberg, S. A., 1985, "Combined-modality therapy of cancer: what is it and when does it work?" New Engl. J. Med. 312:1512-14).

Surgery plays the central role in the diagnosis and treatment of cancer. In general, a surgical approach is required for biopsy, and surgery can be the definitive treatment for most patients with cancer. Surgery is also used to reduce tumor mass, to resect metastases, to resolve medical emergencies, to palliate and rehabilitate. Although the primary surgical technique for cancer treatment has involved the development of an operative field where tumors are resected under direct visualization, current techniques allow for some resections to be performed by endoscopic means. A primary concern in the treatment of cancer is the consideration of operative risk (Stockdale, F., supra).

Radiation therapy plays an important role in both the primary and palliative treatment of cancer. Both teletherapy (megavoltage radiation therapy) and brachytherapy (interstitial and intracavity radiation) are in common use. Electromagnetic radiation in the form of x-rays is most commonly used in teletherapy to treat common malignant tumors, while gamma rays, a form of electromagnetic radiation similar to x-rays but emitted by radioactive isotopes of radium, cobalt, and other elements, are also used. Radiation therapy transfers energy to tissues as discrete packets of energy, called photons, that damage both malignant and normal tissues by producing ionization within cells. The target for the ions is most commonly the DNA; radiation therapy exploits the fact that the radiation damage is not uniform between malignant and non-malignant tissues—rapidly dividing cells are more sensitive to DNA damage than quiescent cells (Pass, H. I., 1993, "Photodynamic therapy in oncology: mechanisms and clinical use," J. Natl. Cancer Instit. 85:443-56.) Radiation therapy is associated with unique benefits as well as important toxicities. Radiation is preferred in certain anatomic areas, (e.g., the mediastinum), where radiation may be the only feasible local method of treatment, and radiation may also be the only feasible local modality if tumor involvement is extensive. Radiation may also be used when the patient finds surgery unacceptable, or when the patient's medical condition prohibits a surgical procedure. Radiation treatment involves tissue damage which can lead to early and late radiation effects. The early effects (acute toxicity of radiation therapy) include erythema of the skin, desquamation, esophagitis, nausea, alopecia, and mylosupression, while the late effects include tissue necrosis and fibrosis, and usually determine the limiting toxicity of radiation therapy (Stockdale, F., supra).

Nearly all chemotherapeutic agents currently in use interfere with DNA synthesis, with the provision of precursors for DNA and RNA synthesis, or with mitosis, and thus target proliferating cells (Stockdale, F., "Cancer growth and chemotherapy," supra). Animal tumor investigation and human clinical trials have shown that drug combinations produce higher rates of objective response and longer survival than single agents (Frei, E. III, 1972, "Combination cancer therapy: presidential address," Cancer Res. 32:2593-2607). Combination drug therapy uses the different mechanisms of action and cytotoxic potentials of multiple drugs, including the alkylating agents, antimetabolites, and antibiotics (Devita, V. T., et al., 1975, "Combination versus single agent chemotherapy: a review of the basis for selection of drug treatment of cancer," Cancer 35:98-110). The physiologic condition of the patient, the growth characteristics of the tumor, the heterogeneity of the tumor cell population, and the multidrug resistance status of the tumor influence the efficacy of chemotherapy. Generally, chemotherapy is not targeted (although these techniques are being developed, e.g. Pastan, I. et al., 1986, "Immunotoxins," Cell 47:641-648), and side effects such as bone marrow depression, gastroenteritis, nausea, alopecia, liver or lung damage, or sterility can result.

Current Treatments—Immunology

The treatment regimes described above have had varying degrees of success. Because the success rate is far from perfect in many cases research continues to develop better treatments. One promising area of research relates to affecting the immune system. By the use of genetic engineering and/or chemical stimulation it is possible to modify and/or stimulate immune responses so that the body's own immune system treats the disease e.g., antibodies destroy cancer cells. This type of treatment departs from those described above in that it utilizes a biological process to fight a disease. However, the treatment is still a treatment that involves giving the patient an active compound not native to the patient.

The present invention can be utilized for treatments which involve a radical departure from normal treatments in that the present invention uses an active compound native to the patient being treated for affecting the cancerous, damaged or inflamed cells.

SUMMARY OF THE INVENTION

A method of treating cancer is disclosed whereby blood is extracted from a patient and platelets in the blood concentrated, e.g. to form platelet-rich plasma (PRP). The concentrated platelets are broken open in processing such as by subjecting them to ultrasound to break the platelets open and obtain platelet releasate. The releasate is formulated into an injectable formulation which is administered directly to the cancer e.g. injected into a tumor. A series of injections of a therapeutically effective amount of the formulation is repeatedly administered to the patient which may be the same patient from which the platelets were extracted. Particular components of the releasate may be concentrated or removed during the formation of the injectable formulation which may include the isolation of a single component or the inclusion of all the naturally occurring components but for a single component or components.

An aspect of the invention is a formulation comprised of a patient's own platelet releasate.

Another aspect of the invention is a method whereby a patient is treated using an injectable formulation of specific molecules (e.g. individual growth factor or cytokine) isolated from the patient being treated.

Yet another aspect of the invention is using a platelet releasate formulation of the invention as an adjunct to be used in combination with one or more conventional cancer methodologies such as surgical removal of cancerous tissue, radiation and chemotherapy.

These and other objects, advantages, and features of the invention will become apparent to those persons skilled in the art upon reading the details of the formulations and methods as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
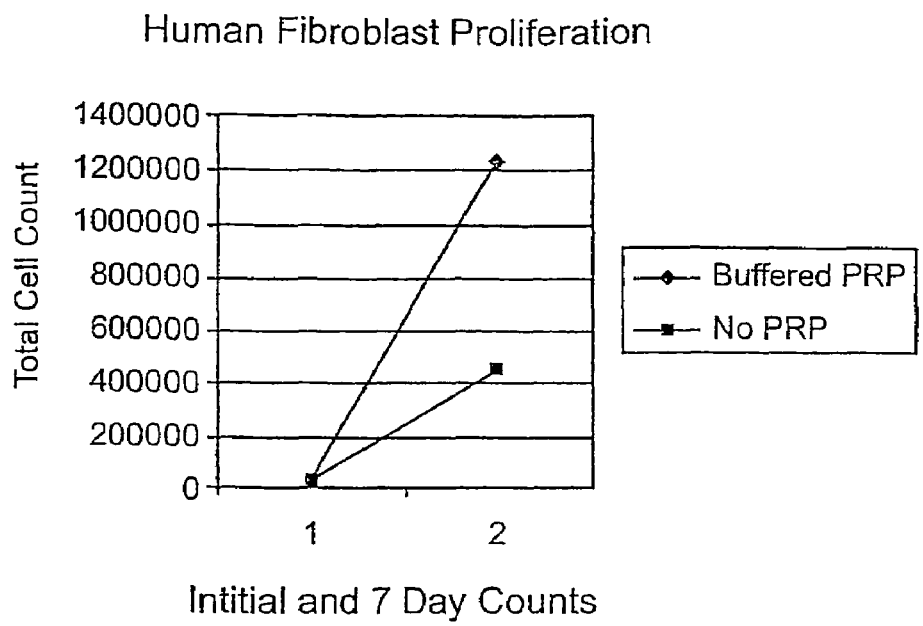
FIG. 1 is a graph of cell count versus time for cultured fibroblast cells in PRP.

Before the present formulations and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a cell" includes a plurality of such cells and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "platelet" is used here to refer to a blood platelet. A platelet can be described as a minisule protoplasmic disk occurring in vertebrate blood. Platelets play a role in blood clotting. The platelet may be derived from any source including a human blood supply, or the patient's own blood. Thus, the platelets in the composition of the inventions may be autologous. The platelets may be homologous, i.e. form a human but not the same human being treated with the composition.

The term "platelet-rich-plasma," "PRP" and the like are used interchangeable here to mean a concentration of platelets in a carrier which concentration is above that of platelets normally found in blood. For example, the platelet concentration may be 5 times, 10 times, 100 times or more the normal concentration in blood. The PRP may use the patient's own plasma as the carrier and the platelets may be present in the plasma at a range of from about 200,000 or less to 2,000,000 or more platelets per cubic centimeter. The PRP may be formed from whole blood e.g. by technology disclosed in any of U.S. Pat. Nos. 5,614,106; 5,580,465; 5,258,126 or publication cited in these patents and if needed stored by technology as taught in 2002/0034722A1; U.S. Pat. No. 5,622,867 or publications cited therein. The PRP may comprise blood component other than platelets. It may be 50% or more, 75% or more, 80% or more, 95% or more, 99% or more platelets. The non-platelet components may be plasma, white blood cells and/or any blood component. PRP is formed from the concentration of platelets from whole blood, and may be obtained using autologous, allogenic, or pooled sources of platelets and/or plasma. PRP may be formed from a variety of animal sources, including human sources.

The "dose" of platelets administered to a patient will vary over a wide range based on the age, weight, sex and condition of the patient as well as the patients' own normal platelet concentration, which as indicated above can vary over a ten fold or greater range. Doses of 1 million to 5 million platelets are typical but may be less or greater than such by a factor of two, five, ten or more.

The term "platelet releasate" is the PRP as defined above but treated so that what is inside the platelet shells is allowed to come out. The releasate may be subjected to processing whereby the platelet shells are removed and/or other blood components are removed, e.g. white blood cells and/or red blood cells or remaining plasma is removed. The pH of the platelet releasate may be adjusted to physiological pH or higher or to about 7.4±10%, 7.4±5%, 7.4±2% or 7.4 to 7.6 as needed.

The terms "treatment", "treating" and the like are used herein to generally mean obtaining a desired pharmacologic, physiologic or cosmetic effect. The effect may be prophylactic in terms of completely or partially preventing a condition, appearance, disease or symptom thereof and/or may be therapeutic in terms of a partial or complete cure for a condition and/or adverse effect attributable to a condition or disease. "Treatment" as used herein covers any treatment of a condition, disease or undesirable appearance in a mammal, particularly a human, and includes:

(a) preventing the disease (e.g. cancer), condition (pain) or appearance (e.g. visable tumors) from occurring in a subject which may be predisposed to such but has not yet been observed or diagnosed as having it;

(b) inhibiting the disease, condition or appearance, i.e., causing regression of condition or appearance.

(c) relieving the disease, condition or undesired appearance, i.e., causing regression of condition or appearance.

The invention includes treating patients with platelet releasate or components thereof formulated in accordance with the invention. Accordingly, the term "treatment" is intended to mean providing a therapeutically detectable and beneficial effect of any kind on a patient.

The terms "synergistic", "synergistic effect" and like are used herein to describe improved treatment effects obtained by combining one or more active components together in a composition or in a method of treatment. Although a synergistic effect in some field is meant an effect which is more than additive (e.g., 1+1=3) in the field of treating many diseases an additive (1+1=2) or less than additive (1+1=1.6) effect may be synergistic. For example, if one active ingredient removed 50% of a disease and a second active ingredient removed 50% of the disease the combined (and merely additional) effect would be 100% removal of the disease. However, the effect of both would not be expected to remove 100% of the disease. Often, two active ingredients have no better or even worse results than either component by itself. If an additive effect could be obtained merely by combining treatments than multiple ingredients could be applied to successfully treat any disease and such is not the case.

Invention in General

The growth of cells is affected by the molecules (e.g. growth factors and cytokines) surrounding and coming into contact with cells and in particular contacting and activating various cellular receptors. Cells respond to particular types of molecules and have their growth and proliferation modulated. The combination of molecules most suitable for modulating cellular growth and proliferation are found in the animal's own platelets as well as other isolated components of blood. In accordance with the invention platelets may be concentrated from blood and sonicated to obtain a releasate and particularly components of the releasate isolated from use in treatments or isolated so that the remainder of the releasate is used in treatment. The white blood cells may be left in the releasate or removed prior to sonication. Further, the white blood cells may be isolated separately and sonicated as a whole or after sorting to isolate a particular class or type of white blood cell. To better understand how cells are affected by the content of platelets, white blood cells and/or other isolated blood components the molecular components that effect cell growth and proliferation are described below.

Platelet Alloimmunization

Platelets present a variety of antigens, including HLA and platelet-specific antigens. Patients transfused with platelets which are not their own often develop HLA antibodies. The patient may become refractory to all but HLA-matched platelets. When platelets are transfused to a patient with an antibody specific for an expressed antigen, the survival time of the transfused platelets may be markedly shortened. Nonimmune events may also contribute to reduced platelet survival. It is possible to distinguish immune from nonimmune platelet refractoriness by assessing platelet recovery soon after infusion, i.e., 10-60 minutes postinfusion platelet increment. In immune refractory states secondary to serologic incompatibility, there is poor recovery in the early postinfusion interval. In nonimmune mechanisms, i.e., splenomegaly, sepsis, fever, intravascular devices, and DIC, platelet recovery within 1 hour of infusion may be adequate while long-term survival (i.e., 24-hour survival) is reduced. Serologic tests may be helpful in selecting platelets with acceptable survival. In accordance with the present invention the platelets are preferably taken from the same patient they will be used to treat. In a similar manner the platelet releasate or any portion thereof is taken from the same patient treated with the formulation. Alternatively, the patient is treated with platelets, platelet releasate and portions thereof extracted from a donor patient tested for and found to have a close serologic match with the patient being treated.

Growth Factors and Cytokines

The following lists some growth factors and cytokines followed by a more detailed description.
Epidermal Growth Factor (EGF)
Platelet-Derived Growth Factor (PDGF)

Fibroblast Growth Factors (FGFs)
Transforming Growth Factors-b TGFs-β)
Transforming Growth Factor-a (TGF-α)
Erythropoietin (Epo)
Insulin-Like Growth Factor-I (IGF-I)
Insulin-Like Growth Factor-II (IGF-II)
Interleukin-1 (IL-1)
Interleukin-2 (IL-2)
Interleukin-6 (IL-6)
Interleukin-8 (IL-8)
Tumor Necrosis Factor-a (TNF-α)
Tumor Necrosis Factor-b (TNF-β)
Interferon-g (INF-γ)
Colony Stimulating Factors (CSFs)

this list is not intended to be comprehensive and the information supplied is only a brief overview.

Growth factors are proteins that bind to receptors on the cell surface, with the primary result of activating cellular proliferation and/or differentiation. Many growth factors are quite versatile, stimulating cellular division in numerous different cell types; while others are specific to a particular cell-type.

Cytokines and growth factors are polypeptide molecules that are present in platelets and regulate migration, proliferation, differentiation and metabolism of mammalian cells. They may act in a paracrine manner on cells adjacent to the secreting cell, as autocrine factors on the secreting cell and also bound to carrier proteins as endocrine factors. A diverse range of these factors have been identified in wound interstitial fluid and a number have been identified as potentially playing a key role in regulating healing which, of course, requires controlled cell growth. Platelet derived growth factor (PDGF) and Transforming Growth Factor (TGF) are released by platelets and are important in initiating healing. The inflammatory phase of healing is modulated by cytokines such as Tumour Necrosis Factor alpha (TNFa), Interleukin-1 (IL-1), Interleukin-4 (IL-4) and the peptide chemokine Interleukin-8 (IL-8). The sequential phases of granulation tissue formation, re-epithelialisation and extracellular matrix formation are regulated by Fibroblast Growth Factors, Transforming Growth Factors and Epidermal Growth Factor and others.

Cytokines are a unique family of growth factors. Secreted primarily from leukocytes, cytokines stimulate both the humoral and cellular immune responses, as well as the activation of phagocytic cells. Cytokines that are secreted from lymphocytes are termed lymphokines, whereas those secreted by monocytes or macrophages are termed monokines. A large family of cytokines are produced by various cells of the body. Many of the lymphokines are also known as interleukins (ILs), since they are not only secreted by leukocytes but also able to affect the cellular responses of leukocytes. Specifically, interleukins are growth factors targeted to cells of hematopoietic origin. The list of identified interleukins grows continuously with the total number of individual activities now at about eighteen.

The term cytokine generally refers to molecules such as the which have initially been investigated for their role in regulation of the immune response. Because of the inflammatory response that is associated with wounded tissue they also have a potential role to play in regulation of healing either directly by their effect on the structural cells in wounded tissue such as fibroblasts, endothelial cells or keratinocytes, or indirectly by their modulation of growth factor production by macrophages.

IL-1 and TNFα are both pro-inflammatory cytokines that will induce expression of adhesion molecules such as ICAM-1 and E-Selectin by endothelial cells allowing leukocytes to adhere to the lumen of capillaries and extravasate into the wound site. These cytokines activate macrophages and initiate production of growth factors required for healing and more pro-inflammatory mediators to prolong the inflammatory response. Overproduction of TNFα may lead to a persisting chronic inflammatory response that is involved in the pathogenesis of chronic wounds. However there is a requirement for TNFα to allow normal healing and induction of a transient TNFα response may re-initiate healing in non-healing chronic wounds.

In order for monocytes to differentiate into activated macrophages they need to pass through a priming stage of differentiation. During this stage they are programmed for responsiveness to subsequent stimuli by exposure to the cytokine microenvironment. For example, interferon-γ will give a positive priming signal whilst exposure to interleukin-4 acts to down regulate the inflammatory response by inhibition of priming.

Platelet Derived Growth Factor

PDGF is a family of three isoforms, composed of dimers of the PDGF-α or PDGF-β chains, which have overlapping but distinct biological properties generated by interaction with two types of receptor. It is produced by platelets, macrophages, endothelial cells and keratinocytes. Release of PDGF by platelets is important in initiating healing. It stimulates chemotaxis of fibroblasts, neutrophils and macrophages. Once these cells are attracted to the wound site PDGF can then activate macrophages and induce proliferation of fibroblasts. Additionally it can stimulate the production of the extracellular matrix components fibronectin and hyaluronan although not as effectively as other factors such as TGFβ.

Recombinant PDGF has been evaluated in several clinical trials to treat non-healing chronic wounds and has been demonstrated to benefit wound healing when healing has been impaired by diabetes. The PDGF of formulations of the invention may be obtained from platelet releasate of the same patient being treated. This releasate PDGF may be supplemented with recombinantly produced PDGF.

PDGF is composed of two distinct polypeptide chains, A and B, that form homodimers (AA or BB) or heterodimers (AB). The c-Sis proto-oncogene has been shown to be homologous to the PDGF A chain. Only the dimeric forms of PDGF interact with the PDGF receptor. Two distinct classes of PDGF receptor have been cloned, one specific for AA homodimers and another that binds BB and AB type dimers. Like the EGF receptor, the PDGF receptors have intrinsic tyrosine kinase activity. Following autophosphorylation of the PDGF receptor, numerous signal-transducing proteins associate with the receptor and are subsequently tyrosine phosphorylated.

Proliferative responses to PDGF action are exerted on many mesenchymal cell types. Other growth-related responses to PDGF include cytoskeletal rearrangement and increased polyphosphoinositol turnover. Again, like EGF, PDGF induces the expression of a number of nuclear localized proto-oncogenes, such as Fos, Myc and Jun. The primary effects of TGF-β are due to the induction, by TGF-β, of PDGF expression.

Epidermal Growth Factor (EGF)

Epidermal growth factor (EGF) is a small molecule which exhibits homology with regions of the TGFα molecule. It is produced by macrophages and epidermal cells with the keratinocyte and fibroblast as targets. Its primary role is to stimulate keratinocytes to migrate across the wound provisional matrix and induce epidermal regeneration.

EGF, like all growth factors, binds to specific high-affinity, low-capacity receptors on the surface of responsive cells. Intrinsic to the EGF receptor is tyrosine kinase activity, which is activated in response to EGF binding. The kinase domain of the EGF receptor phosphorylates the EGF receptor itself (autophosphorylation) as well as other proteins, in signal transduction cascades, that associate with the receptor following activation. Experimental evidence has shown that the Neu proto-oncogene is a homologue of the EGF receptor.

EGF has proliferative effects on cells of both mesodermal and ectodermal origin, particularly keratinocytes and fibroblasts. EGF exhibits negative growth effects on certain carcinomas as well as hair follicle cells. Growth-related responses to EGF include the induction of nuclear proto-oncogene expression, such as Fos, and Myc. EGF also has the effect of decreasing gastric acid secretion.

Fibroblast Growth Factors (FGFS)

There are at least 14 distinct members of the FGF family of growth factors. The two originally characterized FGFs were identified by biological assay and are termed FGF1 (acidic-FGF, aFGF) and FGF2 (basic-FGF, bFGF). Kaposi's sarcoma cells (prevalent in patients with AIDS) secrete a homologue of FGF called the K-FGF proto-oncogene. In mice the mammary tumor virus integrates at two predominant sites in the mouse genome identified as Int-1 and Int-2. The protein encoded by the Int-2 locus is a homologue of the FGF family of growth factors.

Studies of human disorders as well as gene knock-out studies in mice show the prominent role for FGFs is in the development of the skeletal system and nervous system in mammals. FGFs also are neurotrophic for cells of both the peripheral and central nervous system. Additionally, several members of the FGF family are potent inducers of mesodermal differentiation in early embryos. Non-proliferative effects include regulation of pituitary and ovarian cell function.

The FGFs interact with specific cell-surface receptors. There have been identified 4 distinct receptor types identified as FGFR1-FGFR4. Each of these receptors has intrinsic tyrosine-kinase activity like both the EGF and PDGF receptors. As with all transmembrane receptors that have tyrosine kinase activity, autophosphorylation of the receptor is the immediate response to FGF binding. Following activation of FGF receptors, numerous signal-transducing proteins associate with the receptor and become tyrosine-phosphorylated. The Flg proto-oncogene is a homologue of the FGF receptor family. The FGFR1 receptor also has been shown to be the portal of entry into cells for herpes viruses. FGFs also bind to cell-surface heparan-sulfated proteoglycans with low affinity relative to that of the specific receptors. The purpose in binding of FGFs to theses proteoglycans is not completely understood but may allow the growth factor to remain associated with the extracellular surface of cells that they are intended to stimulate under various conditions. The FGF receptors are widley expressed in developing bone and several common autosomal dominant disorders of bone growth have been shown to result from mutations in the FGFR genes. The most prevalent is achondroplasia, ACH. ACH is characterized by disproportionate short stature, where the limbs are shorter than the trunk, and macrocephaly (excessive head size). Almost all persons with ACH exhibit a glycine to arginine substitution in the transmembrane domain of FGFR3. This mutation results in ligand-independent activation of the receptor. FGFR3 is predominantly expressed in quiescent chondrocytes where it is responsible for restricting chondrocyte proliferation and differentiation. In mice with inactivating mutations in FGFR3 there is an expansion of long bone growth and zones of proliferating cartilage further demonstrating that FGFR3 is necessary to control the rate and amount of chondrocyte growth. Several other disorders of bone growth collectively identified as craniosynostosis syndromes have been shown to result from mutations in FGFR1, FGFR2 and FGFR3. Sometimes the same mutation can cause two or more different craniosynostosis syndromes. A cysteine to tyrosine substitution in FGFR2 can cause either Pfeiffer or Crouzon syndrome. This phenomenon indicates that additional factors are likely responsible for the different phenotypes.

Affected Receptor Syndrome Phenotypes

FGFR1 Pfeiffer broad first digits, hypertelorism

FGFR2 Apert mid-face hypoplasia, fusion of digits

FGFR2 Beare-Stevenson mid-face hypoplasia, corrugated skin

FGFR2 Crouzon mid-face hypoplasia, ocular proptosis

FGFR2 Jackson-Weiss mid-face hypoplasia, foot anamolies

FGFR2 Pfeiffer same as for FGFR1 mutations

FGFR3 Crouzon mid-face hypoplasia, acanthosis nigricans, ocular proptosis

FGFR3 Non-syndromatic craniosynostosis digit defects, hearing loss

Trasforming Growth Factors-$\beta$ (TGFS-$\beta$)

The three isoforms of TGF$\beta$($\beta$1, $\beta$2 and $\beta$3) have a broad range of activity within healing. TGF$\beta$1 is the most abundant in all tissues and is the form found in platelets.

All cells involved in healing can produce and/or respond to TGF$\beta$.

Release of TGF$\beta$ by platelets at the same time as PDGF is important in initiating healing as, at low concentrations, it is chemotactic for monocytes, lymphocytes, and fibroblasts. Its role in angiogenesis is controversial as in some experimental systems it stimulates endothelial cell proliferation and tubule formation whilst in others it is inhibitory. Its actions may therefore be contextual and concentration dependent.

TGF$\beta$ plays a central role in regulating maturation and strength of of tissues involved in wound healing. It regulates many matrix proteins including collagen, proteoglycans, fibronectin, matrix degrading proteases and their inhibitors. Topical application of TGF$\beta$ increases the strength of experimental incisional wounds. Manipulation of the TGF$\beta$ isoforms during healing can modify scarring. Antibody neutralisation of TGFP$\beta$1 and $\beta$2 or increasing TGF$\beta$3 concentrations by exogenous application decreases post surgical scarring.

TGF-$\beta$ was originally characterized as a protein (secreted from a tumor cell line) that was capable of inducing a transformed phenotype in non-neoplastic cells in culture. This effect was reversible, as demonstrated by the reversion of the cells to a normal phenotype following removal of the TGF-$\beta$. Subsequently, many proteins homologous to TGF-$\beta$ have been identified. The four closest relatives are TGF-$\beta$-1 (the original TGF-$\beta$) through TGF-$\beta$-5 (TGF-$\beta$-1=TGF-$\beta$-4). All four of these proteins share extensive regions of similarity in their amino acids. Many other proteins, possessing distinct biological functions, have stretches of amino-acid homology to the TGF-$\beta$ family of proteins, particularly the C-terminal region of these proteins.

The TGF-β-related family of proteins includes the activin and inhibin proteins. There are activin A, B and AB proteins, as well as an inhibin A and inhibin B protein. The Mullerian inhibiting substance (MIS) is also a TGF-β-related protein, as are members of the bone morphogenetic protein (BMP) family of bone growth-regulatory factors. Indeed, the TGF-β family may comprise as many as 100 distinct proteins, all with at least one region of amino-acid sequence homology.

There are several classes of cell-surface receptors that bind different TGFs-β with differing affinities. There also are cell-type specific differences in receptor sub-types. Unlike the EGF, PDGF and FGF receptors, the TGF-β family of receptors all have intrinsic serine/threonine kinase activity and, therefore, induce distinct cascades of signal transduction.

TGFs-β have proliferative effects on many mesenchymal and epithelial cell types. Under certain conditions TGFs-β will demonstrate anti-proliferative effects on endothelial cells, macrophages, and T- and B-lymphocytes. Such effects include decreasing the secretion of immunoglobulin and suppressing hematopoiesis, myogenesis, adipogenesis and adrenal steroidogenesis. Several members of the TGF-β family are potent inducers of mesodermal differentiation in early embryos, in particular TGF-β and activin A.

Transforming Growth Factor-α (TGF-α)

TGF-α, like the β form, was first identified as a substance secreted from certain tumor cells that, in conjunction with TGF-β-1, could reversibly transform certain types of normal cells in culture. TGF-α binds to the EGF receptor, as well as its own distinct receptor, and it is this interaction that is thought to be responsible for the growth factor's effect. The predominant sources of TGF-α are carcinomas, but activated macrophages and keratinocytes (and possibly other epithelial cells) also secrete TGF-α. In normal cell populations, TGF-α is a potent keratinocyte growth factor; forming an autocrine growth loop by virtue of the protein activating the very cells that produce it.

Erythropoietin (Epo)

Epo is synthesized by the kidney and is the primary regulator of erythropoiesis. Epo stimulates the proliferation and differentiation of immature erythrocytes; it also stimulates the growth of erythoid progenitor cells (e.g. erythrocyte burst-forming and colony-forming units) and induces the differentiation of erythrocyte colony-forming units into pro-erythroblasts. When patients suffering from anemia due to kidney failure are given Epo, the result is a rapid and significant increase in red blood cell count.

Insulin-Like Growth Factor-I (IGF-I)

IGF-I (originally called somatomedin C) is a growth factor structurally related to insulin. IGF-I is the primary protein involved in responses of cells to growth hormone (GH): that is, IGF-I is produced in response to GH and then induces subsequent cellular activities, particularly on bone growth. It is the activity of IGF-I in response to GH that gave rise to the term somatomedin. Subsequent studies have demonstrated, however, that IGF-I has autocrine and paracrine activities in addition to the initially observed endocrine activities on bone. The IGF-I receptor, like the insulin receptor, has intrinsic tyrosine kinase activity. Owing to their structural similarities IGF-I can bind to the insulin receptor but does so at a much lower affinity than does insulin itself.

Insulin-Like Growth Factor-II (IGF-II)

IGF-II is almost exclusively expressed in embryonic and neonatal tissues. Following birth, the level of detectable IGF-II protein falls significantly. For this reason IGF-II is thought to be a fetal growth factor. The IGF-II receptor is identical to the mannose-6-phosphate receptor that is responsible for the integration of lysosomal enzymes (which contain mannose-6-phosphate residues) to the lysosomes.

Interleukin-1 (IL-1)

IL-1 is one of the most important immune response—modifying interleukins. The predominant function of IL-1 is to enhance the activation of T-cells in response to antigen. The activation of T-cells, by IL-1, leads to increased T-cell production of IL-2 and of the IL-2 receptor, which in turn augments the activation of the T-cells in an autocrine loop. IL-1 also induces expression of interferon-g (IFN-g) by T-cells. This effect of T-cell activation by IL-1 is mimicked by TNF-a which is another cytokine secreted by activated macrophages. There are 2 distinct IL-1 proteins, termed IL-1-a and -1-b, that are 26% homologous at the amino acid level. The IL-1 is are secreted primarily by macrophages but also from neutrophils, endothelial cells, smooth muscle cells, glial cells, astrocytes, B- and T-cells, fibroblasts and keratinocytes. Production of IL-1 by these different cell types occurs only in response to cellular stimulation. In addition to its effects on T-cells, IL-1 can induce proliferation in non-lymphoid cells.

Interleukin-2 (IL-2)

IL-2, produced and secreted by activated T-cells, is the major interleukin responsible for clonal T-cell proliferation. IL-2 also exerts effects on B-cells, macrophages, and natural killer (NK) cells. The production of IL-2 occurs primarily by CD4+ T-helper cells. As indicated above, the expression of both IL-2 and the IL-2 receptor by T-cells is induced by IL-1. Indeed, the IL-2 receptor is not expressed on the surface of resting T-cells and is present only transiently on the surface of T-cells, disappearing within 6-10 days of antigen presentation. In contrast to T-helper cells, NK cells constitutively express IL-2 receptors and will secrete TNF-a, IFN-g and GM-CSF in response to IL-2, which in turn activate macrophages.

Interleukin-6 (IL-6)

IL-6 is produced by macrophages, fibroblasts, endothelial cells and activated T-helper cells. IL-6 acts in synergy with IL-1 and TNF-a in many immune responses, including T-cell activation. In particular, IL-6 is the primary inducer of the acute-phase response in liver. IL-6 also enhances the differentiation of B-cells and their consequent production of immunoglobulin. Glucocorticoid synthesis is also enhanced by IL-6. Unlike IL-1, IL-2 and TNF-a, IL-6 does not induce cytokine expression; its main effects, therefore, are to augment the responses of immune cells to other cytokines.

Interleukin-8 (IL-8)

IL-8 is an interleukin that belongs to an ever-expanding family of proteins that exert chemoattractant activity to leukocytes and fibroblasts. This family of proteins is termed the chemokines. IL-8 is produced by monocytes, neutrophils, and NK cells and is chemoattractant for neutrophils, basophils and T-cells. In addition, IL-8 activates neutrophils to degranulate.

Tumor Necrosos Factor-α (TNF-α)

TNF-α(also called cachectin), like IL-1 is a major immune response-modifying cytokine produced primarily by activated macrophages. Like IL-1, TNF-α induces the expression of other autocrine growth factors, increases cellular responsiveness to growth factors and induces signaling pathways that lead to proliferation. TNF-α acts synergistically with EGF and PDGF on some cell types. Like other growth factors, TNF-α induces expression of a number of nuclear proto-oncogenes as well as of several interleukins.

Tumor Necrosis Factor-β (TNF-β)

TNF-β (also called lymphotoxin) is characterized by its ability to kill a number of different cell types, as well as the ability to induce terminal differentiation in others. One significant non-proliferative response to TNF-β is an inhibition of lipoprotein lipase present on the surface of vascular endothelial cells. The predominant site of TNF-β synthesis is T-lymphocytes, in particular the special class of T-cells called cytotoxic T-lymphocytes (CTL cells). The induction of TNF-β expression results from elevations in IL-2 as well as the interaction of antigen with T-cell receptors.

Interferon-G (INF-γ)

IFN-α, IFN-β and IFN-μ are known as type I interferons: they are predominantly responsible for the antiviral activities of the interferons. In contrast, IFN-γ is a type II or immune interferon. Although IFN-γ, has antiviral activity it is significantly less active at this function than the type I IFNs. Unlike the type I IFNs, IFN-γ is not induced by infection nor by double-stranded RNAs. IFN-γ is secreted primarily by CD8+ T-cells. Nearly all cells express receptors for IFN-γ0 and respond to IFN-γ binding by increasing the surface expression of class I MHC proteins, thereby promoting the presentation of antigen to T-helper (CD4+) cells. IFN-γ also increases the presentation of class II MHC proteins on class II cells further enhancing the ability of cells to present antigen to T-cells.

Colony Stimulating Factors (CSFs)

CSFs are cytokines that stimulate the proliferation of specific pluripotent stem cells of the bone marrow in adults. Granulocyte-CSF (G-CSF) is specific for proliferative effects on cells of the granulocyte lineage. Macrophage-CSF (M-CSF) is specific for cells of the macrophage lineage. Granulocyte-macrophage-CSF (GM-CSF) has proliferative effects on both classes of lymphoid cells. Epo is also considered a CSF as well as a growth factor, since it stimulates the proliferation of erythrocyte colony-forming units. IL-3 (secreted primarily from T-cells) is also known as multi-CSF, since it stimulates stem cells to produce all forms of hematopoietic cells.

Other Factors

Other factors are involved in the regulation of cell growth and proliferation including Vascular Endothelial Cell Growth Factor (VEGF), Insulin Like Growth Factor (IGF-1), Granulocyte Monocyte Colony Stimulating Factor (GM-CSF).

Methodology/Radiation

In accordance with the invention blood is extracted from a patient and platelets from the blood are concentrated. The platelets are processed in a manner so as to open the platelets and allow the platelet releasate to come out. The platelet releasate is then formulated such as by adding a buffering agent to adjust the pH to about 7.4±10% or ±5% or ±2% or ±1%. The processing of the platelets may be carried out by exposing the platelets to energy waves, agitation, chemical treatments, heat or other means so as to open the platelets and allow the releasate to come out. Preferably 90% or more of the platelets are opened, or 95% or more or substantially all of the platelets are opened. The platelet coverings may be removed or may become part of the releasate formulation which is buffered to a preferred pH range. The platelet releasate may be formulated with various salts in an aqueous injectable formulation which is administered to a patient. The patient is preferably the same patient from which the blood is extracted and the platelets are obtained.

When formulating the formulation it is possible to subject the formulation to various protein separation technologies including high pressure gas chromatography (HPGC) or high pressure liquid chromatography (HPLC) and the like or a variety of different protein separation technologies known to those skilled in the art. This can be done in order to separate out one or more of the growth factors, cytokines or other proteins present within the releasate. It is also possible to supplement the releasate by adding one or more proteins, growth factors, cytolines or other compounds to improve the therapeutic ability of the formulation. It is possible to separate away only a single growth factor, cytokine or protein. It is also possible to separate 2, 3 or any number of different components away from the platelet releasate. In addition, it is possible to add components which are not present or to supplement the percentage amount of proteins, growth factors and cytokines present with those which have been recombinantly produced. Thus, by combining different components in terms of growth factors, cytokines, proteins, etc. together a mixture can be tailored to treat the patient's particular cancer.

Platelet releasate is shown to have an effect on cellular growth within the examples such as Examples 5 and 6 below. Those skilled in the art will understand that by taling tissue samples from the patient including tissue samples from a cancerous tumor it is possible to test different formulations on the tissue sample in order to determine the effect on the tissue.

In one aspect of the invention the patient is treated with a combination of the platelet releasate and convention radiation therapy. More specifically, bone marrow cells are extracted from a patient that has been diagnosed as having cancer. Those bone marrow cells are placed on a cell culture medium which culture medium has been supplemented with platelet releasate or a portion of platelet releasate such as described above. The bone marrow cells are allowed to grow on the culture medium supplemented with the platelet releasate as described in detail within Example 7.

The patient from which the bone marrow cells were extracted is then subjected to intense radiation. The radiation treatments are intended to kill the patient's cancer cells. However, the radiation is sufficiently intense such that bone marrow cells of the patient are also destroyed making it substantially impossible for the patient to survive in the absence of new bone marrow cells. Accordingly, after the radiation has proceeded, and the cancer cells within the patient have been allowed to be confirmed as destroyed, the bone marrow cells which have been grown on the platelet releasate supplemented culture medium are formulated into an injectable formulation and readministered to the patient. Those bone marrow cells are allowed to grow in the patient. It is possible that the platelet releasate used to culture the bone marrow cells is platelet releasate obtained from the same patient.

Alternatively, the releasate may be obtained from a healthy patient not suffering from cancer having been tested with various serological tests to provide the best possible match for the patient being treated.

Methodology/Surgery

In accordance with the invention surgery and formulations of the invention can be used together in the treatment of cancer. More specifically, blood is extracted from a patient and platelets are concentrated. The platelets are processed so as to obtain a releasate and the resulting releasate is formulated into an injectable formulation with the addition of a buffering agent in order to adjust the pH as indicated above. The platelets may be obtained from the patient suffering from cancer or may be obtained from a healthy patient which has been tested against the patient being treated in order to determine that a range of matches occur with respect to the patient's serological typing.

When an appropriate formulation comprising platelet releasate has been prepared a patient is subjected to a conventional surgery technique in order to surgically remove the cancerous tumor. After removal of the tumor the area where the tumor was removed from is treated with the platelet releasate formulation of the invention. This is beneficial in a number of different ways. The platelet releasate can aid in improving wound healing. Further, the releasate can aid in modulating the inflammatory response. Lastly, the releasate can aid in modulating the growth of any cancer cells not removed surgically.

Thereafter, the patient may be repeatedly treated with the platelet releasate formulation of the invention by periodically administering the formulation to the patient and, for example, specifically administering the formulation directly to the area for which the tumor was removed. The formulation may be a formulation from which the platelet shells are removed and/or from which one or more of the components of the releasate have been removed. Alternatively, the formulation may be supplemented with one or more pharmaceutically active components such as recombinantly produced growth factors or cytokines. In addition, the formulation may contain other small molecules such as anti-inflammatory agents, antibiotics, anesthetics and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

PRP was prepared using a centrifuge unit made by Harvest (Plymouth, Mass.). (Similar units are available as The Biomet GPS system, the Depuy Symphony machine and the Medtronic Magellan machine.) Approximately 55 cc of blood was drawn from the patient using a standard sterile syringe, combined with 5 cc of a citrate dextrose solution for anticoagulation, and then spun down to isolate the platelets according to the manufacturer's protocol. These platelets were then resuspended in approximately 3 cc of plasma. The resulting platelet rich plasma solution (PRP) was quite acidic and was neutralized with using approximately 0.05 cc of an 8.4% sodium bicarbonate buffer per cc of PRP under sterile conditions to approximately physiologic pH of 7.4. The PRP was not activated through addition of exogenous activators. This PRP composition is referred to herein as autologous platelet extract (APEX).

Example 2

Fifty cc of whole blood is drawn from a patient, and then prepared according to the method of Knighton, U.S. Pat. No. 5,165,938, column 3. The PRP is activated according to Knighton using recombinant human thombin. The degranulated platelets are spun down and the releasate containing supernatant is recovered. The releasate may be optionally pH adjusted to a pH of 7.4 using sodium bicarbonate buffer.

Example 3

Thirty ml of whole blood were drawn from a patient. A platelet composition was prepared according to Example 1 of U.S. Pat. No. 5,510,102 to Cochrum, incorporated herein by reference in its entirety, except that no alginate is added to the platelet composition.

Example 4

Cell Cultures of Any Tissue

A researcher or clinician wishes to grow a cell culture of either fibroblasts or osteoarthritic cartilage cells. Using the technique of Example 1, an autologous platelet extract (APEX) is obtained and buffered to physiologic pH.

The cells are then isolated and grown in a media rich in the APEX in various conditions and dilutions. The APEX promotes cell differentiation and production of proteins such as collagen. The APEX may augment or promote the ability of the cells to transform into normal cells. Without intending to be limited by theory, it is hypothesized the APEX may convert the osteoarthritic cartilage cells to a more functional cell line that is reinjected into a diseased or injured joint. Alternatively, the APEX is directly introduced into an osteoarthritic joint to reverse the course of the disease. This is done under local anesthesia in a sterile manner.

Example 5

Human Fibroblast Proliferation in Buffered Platelet Rich Plasma

Platelet rich plasma has been used to augment bone grafting and to help accelerate or initiate wound healing. Fibroblasts are important components of the wound healing process. This example shows that human fibroblast cells will proliferate more in fetal bovine serum that has been augmented with a proprietary formulation of buffered platelet rich plasma.

Human fibroblasts were isolated and then put into culture with 10% fetal bovine serum that had been augmented with a proprietary formulation of buffered platelet rich plasma (Group 1) or in 10% fetal bovine serum alone (Group 2). Initial cell counts were 25,000 in both groups.

Seven days after initiating the culture experiment, the cells in each group were counted. The average total cell count in Group 1 (buffered PRP added) was 1,235,000. The average total cell count in Group 2 (No PRP) was 443,000. The group that was augmented with the buffered platelet rich plasma of the invention had 2.8 times the proliferation of the control group at seven days. (See FIG. 1)

Buffered platelet rich plasma augments human fibroblast proliferation when compared to the use of fetal bovine serum alone. This has significant implications for the use of buffered platelet rich plasma for either acute or chronic wound healing.

Example 6

Human Fibroblast Proliferation in Sonicated Platelet Rich Plasma

Human fibroblasts were isolated and then put into four different cultures. Three of the cultures comprised 10% fetal bovine serum that had been augmented with 9 uL, 46 uL, and 95 uL of buffered and sonicated platelet rich plasma. The fourth served as the control and was comprised of 10% fetal bovine serum. Initial cell counts were 20,000 in both groups. Variable doses of the sonicated PRP (sPRP) were seeded with cells.

Figure 2:
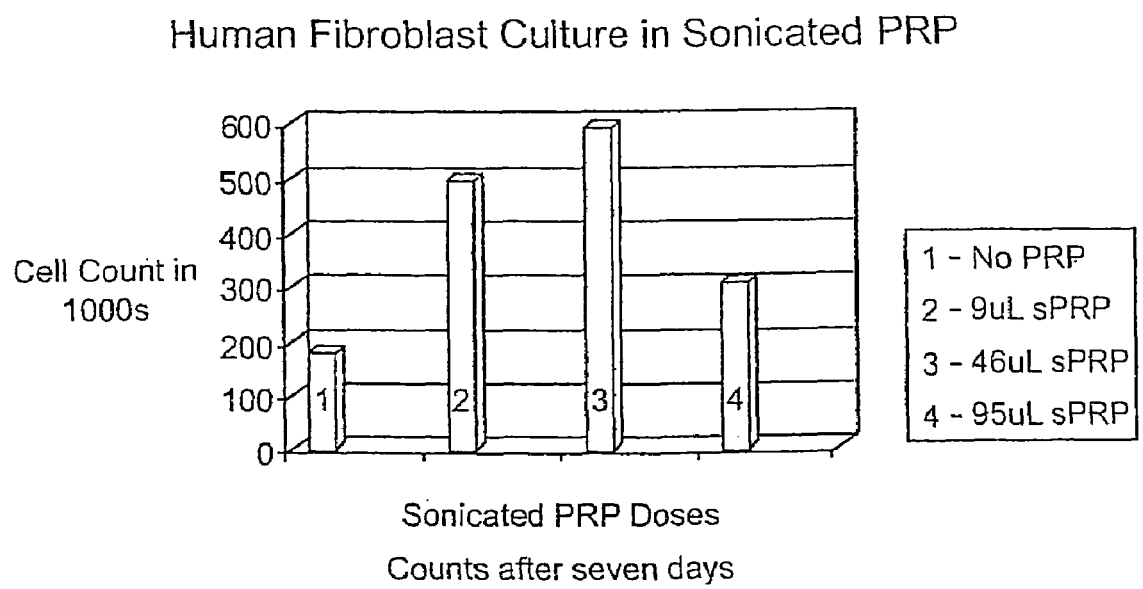
FIG. 2 is a graph of cell count for three different concentrations of PRP releasate and a control.

Four days after initiating the culture experiment, the cells in each of the four groups were counted and the results are shown in FIG. 2. The cell count in the control group (No PRP) was 180,000 cells. The cell counts in the sonicated PRP group were as follows: 496,000 (9 uL dose of sPRP), 592,000 (46 uL dose of sPRP) and 303,000 (95 uL dose of sPRP).

This experiment shows that buffered, and sonicated platelet rich plasma augments human fibroblast proliferation when compared to the use of fetal bovine serum alone.

Example 7

Human Fibroblast Proliferation in Sonicated Platelet Rich Plasma

Human fibroblasts were isolated and then put into different cultures. One of the cultures comprised 10% fetal bovine serum that had been augmented with buffered and sonicated platelet rich plasma. The other served as the control and was comprised of 10% fetal bovine serum. Initial cell counts were 20,000 in both groups.

Figure 3:
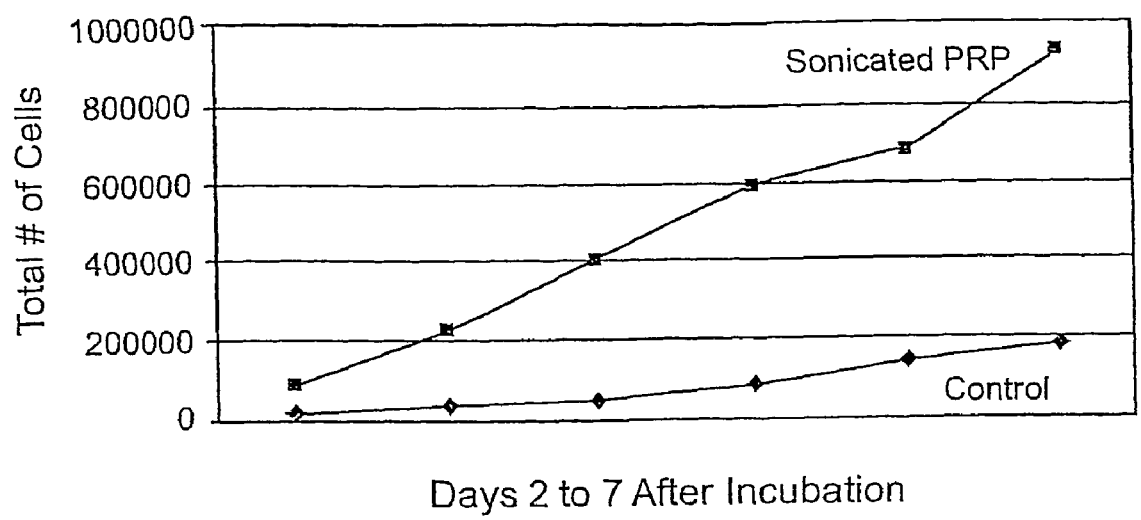
FIG. 3 is a graph of cell counts over seven days for a control and a culture with sonicated PRP.

Seven days after initiating the culture experiment, the cells in each of the two groups were counted and the results are shown in FIG. 3. The cell count in the control group (No PRP) was 183,600 cells. The cell count in the sonicated PRP group was 924,800 cells.

This experiment shows that buffered, and sonicated platelet rich plasma augments human fibroblast proliferation when compared to the use of fetal bovine serum alone. These results show the ability of the platelet releasate to promote cell growth and in particular fibroblast cells which are essential to firm, young looking skin.

Example 8

Prophetic Materials and Methods

Animals

Adult male and female CBA/J mice are obtained from a lab such as the Jackson Laboratory (Bar Harbor, Me.). All mice can be bred and maintained in an appropriate animal facility. Animals used may be 12 to 20 weeks old.

Cultures

Bone marrow cells are collected by flushing the tibias and femurs of CBA/J mice with modified Dulbecco's phosphate-buffered saline (PBS) using a sterile syringe and 25-gauge needle. Homogenous single-cell suspensions are obtained by the repeated passage of cell mixtures through a Pasteur pipet. All cells are washed twice by centrifugation at 250 g for 10 min in PBS and then assessed for viability by trypan blue dye exclusion. Cells are then adjusted to the desired concentration prior to use. Bone marrow cells (250,000) are cultured in 96-well round-bottom microtiter plates ,e.g. (Flow Laboratories, Mississauga, Ontario, Canada). The culture medium may be serum-free RPMI plus 4 mM L-glutamine, 20 mM Hepes, 100 U/ml penicillin, 100 .mu.g/ml streptomycin (GIBCO Laboratories, Burlington, Ontario, Canada), 5 .mu.g/ml transferrin, and $5 \times 10^5$ 2-mercaptoethanol (Eastman Chemicals Co., Rochester N.Y.). Cells are cultured in the presence or absence of PRP and/or releasate at a concentration of 400 .mu.g/ml, respectively. Total volume of all cultures may be 0.2 ml. Cultures are maintained at 37° C. in 95% humidified air and 5% $CO_2$. Six hours prior to harvesting, the cultures are pulsed with 1 μ Ci tritiated thymidine (NEN, sp act 77.1 Ci/mmol). Cells are then harvested on glass fiber mats (Flow Labs) with a multiple sample harvester (Skatron, Flow Labs). Water-insoluble tritiated thymidine incorporation is measured with an LKB 1215 Rackbeta II using standard liquid scintillation techniques.

PRP

PRP or Releasate is Produced as Per Examples 1-3

Results

The effects of PRP on cultured murine bone marrow may be evaluated in serum-free medium. In this experiment, $2.5 \times 10^5$ viable cells from bone marrow of CBA/J mice may be cultured for 72 hours in serum-free RPMI media in the presence or absence of PRP at a final concentration of 400 .mu.g/ml and transferrin at a final concentration of 5 .mu.g/ml.

Therapy

As demonstrated in Examples 5 and 6 PRP and releasate are each effective in promoting the proliferation of cells and accordingly useful for therapy involving the promotion of cell proliferation. This suggests it is useful in the proliferation of bone marrow cells, which would be useful in the treatment for the prevention of side effects of immunosuppressive therapy, radiotherapy or chemotherapy, or other therapies known to depress the immune system and suppress bone marrow production, causing myelotoxicity. Accordingly, PRP and/or releasate is employed to treat deficiencies in hematopoietic progenitor or stem cells, or related disorders.

PRP and/or platelet releasate may also be employed in methods for treating cancer and other pathological states resulting in myclotoxcity, exposure to radiation or drugs, and including for example, leukopenia, bacterial and viral infections, anemia, B cell or T cell deficiencies, including immune cell or hematopoietic cell deficiency following autologous or non-autologous bone marrow transplantation. PRP and/or platetet releasate may also be employed to stimulate development of megakaryocytes and natural killer cells in vitro or in vivo.

The media, compositions, and methods of the invention are also useful for treating cancers that are treated by bone marrow transplants (BMT) that involve removing bone marrow cells from the patient, maintaining these cells in an ex vivo culture while the patient is treated with radiation or chemotherapy, and then transplanting these cells back into the patient after the treatment has been completed to restore the patient's bone marrow. Accordingly, PRP and/or platelet releasate may be employed for BMT as a means for reconstituting bone marrow in ex vivo cell culture medium and for promoting bone marrow cell proliferation in vivo. PRP and/or platelet releasate is also useful for other cell therapies, e.g. cell expansion and/or gene therapy protocols, therapies requiring ex vivo cell culture. PRP and/or platelete releasate is also useful in the prevention of autolocous or allogenic bone marrow transplant rejection.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for treating glioblastoma cancer comprising:
   extracting blood from a patient in need of cancer treatment;
   concentrating platelets from the blood;
   processing the platelets in a manner which breaks open the platelets and obtaining an injectable platelet releasate;
   formulating the platelet releasate into an injectable formulation buffered to a pH of $7.4\pm5\%$; and
   injecting the platelet releasate to the patient in need of said glioblastoma cancer treatment.

2. The method of claim 1, wherein the processing comprises exposing the platelets to energy waves.

3. The method of claim 1, wherein the administering comprises injecting the platelet releasate into a tumor of the patient.

4. The method of claim 1, wherein the administering comprises injecting the platelet releasate into a cancerous tumor of the patient.

5. The method of claim 1, wherein the patient treated with the formulation is the same patient from which the blood is extracted from, and the formulation is buffered to pH $7.4\pm2\%$; and wherein the platelets are processed for a period of time and under conditions so as to break open 90% or more of the platelets.

6. The method of claim 5, further comprising:
   repeatedly injecting a therapeutically effective amount of the formulation to the patient over a period of time while monitoring the patient and adjusting dosing to effectively treat the cancer.

7. The method of claim 1, wherein injecting of the injectable platelet releasate is to an area where a tumor has been removed from the patient.

* * * * *

UNITED STATES PATENT AND TRADEMARK OFFICE
CERTIFICATE OF CORRECTION

PATENT NO. : 7,678,780 B2  Page 1 of 2
APPLICATION NO. : 10/581577
DATED : March 16, 2010
INVENTOR(S) : Allan Mishra It is certified that error appears in the above-identified patent and that said Letters Patent is hereby corrected as shown below:

Sheet 1 of Drawings (FIG. 1), Below X Axis, "Intitial and 7 Day Counts" should be changed to
--Initial and 7 Day Counts--

Column 2, Line 42, "and mylosupression," should be changed to --and myelosuppression,--

Column 4, Line 57, "as a minisule protoplasmic" should be changed to --as a miniscule protoplasmic--

Column 7, Line 58, "which have initially" should be changed to --interleukins which have initially--

Column 8, Line 2, "lumen of capilleries" should be changed to --lumen of capillaries--

Column 9, Line 18, "such as Fos, and Myc." should be changed to --such as Fos, Jun and Myc.--

Column 9, Line 60, "widley expressed in" should be changed to --widely expressed in--

Column 10, Lines 23-24, "foot anamolies" should be changed to --foot anomalies--

Column 10, Line 31, "Trasforming Growth Factors-$\beta$ (TGFS-$\beta$)" should be changed to
--Transforming Growth Factors-$\beta$ (TGFS-$\beta$)--

Column 10, Line 46, "strength of of tissues" should be changed to --strength of tissues--

Column 11, Line 46, "growth of erythoid" should be changed to --growth of erythroid--

Column 12, Line 23, "The IL-1 is are" should be changed to --The IL1s are--

Column 13, Line 1, "Tumor Necrosos Factor-$\alpha$ (TNF-$\alpha$)" should be changed to
--Tumor Necrosis Factor-$\alpha$ (TNF-$\alpha$)--

Column 13, Line 35, "for IFN-$\gamma$0 and" should be changed to --for IFN-$\gamma$ and--

Column 14, Line 26, "cytolines or other" should be changed to --cytokines or other--

Column 14, Line 39, "that by taling tissue" should be changed to --that by taking tissue--

Column 16, Line 18, "human thombin." should be changed to --human thrombin.--

Column 18, Line 60, "resulting in myclotoxcity," should be changed to --resulting in myelotoxicity,--

Signed and Sealed this

Seventeenth Day of August, 2010

David J. Kappos
*Director of the United States Patent and Trademark Office*

Column 18, Line 65, "platetet releasate may" should be changed to --platelet releasate may--

Column 19, Line 15, "and/or platelete releasate" should be changed to --and/or platelet releasate--

Column 19, Line 16, "prevention of autolocous" should be changed to --prevention of autologous--